(12) United States Patent
Zhou et al.

(10) Patent No.: US 10,766,987 B2
(45) Date of Patent: Sep. 8, 2020

(54) CROSSLINKED POLYOLEFINS FOR BIOMEDICAL APPLICATIONS AND METHOD OF MAKING SAME

(71) Applicant: Innolene LLC, Miami, FL (US)

(72) Inventors: Yonghua Zhou, Katy, TX (US); Leonard Pinchuk, Miami, FL (US)

(73) Assignee: Innolene LLC, Miami, FL (US)

( * ) Notice: Subject to any disclaimer, the term of this patent is extended or adjusted under 35 U.S.C. 154(b) by 234 days.

(21) Appl. No.: 15/861,608

(22) Filed: Jan. 3, 2018

(65) Prior Publication Data
US 2018/0127525 A1    May 10, 2018

Related U.S. Application Data

(63) Continuation of application No. 15/202,239, filed on Jul. 5, 2016, now abandoned, which is a continuation (Continued)

(51) Int. Cl.
*C08F 212/32* (2006.01)
*C08F 210/10* (2006.01)
(Continued)

(52) U.S. Cl.
CPC .......... *C08F 210/10* (2013.01); *A61F 2/1613* (2013.01); *A61L 27/16* (2013.01);
(Continued)

(58) Field of Classification Search
CPC ............................ C08F 210/10; C08F 212/32
See application file for complete search history.

(56) References Cited

U.S. PATENT DOCUMENTS 4,622,375 A   11/1986  Wong
4,667,004 A    5/1987  Wong
(Continued)

FOREIGN PATENT DOCUMENTS

CN        1705712      12/2005
WO   WO 2004/035680    4/2004
(Continued)

OTHER PUBLICATIONS

D. Braun, H. Cherdron, M. Rehahn, H. Ritter, and B. Voit. Polymer Synthesis: Theory and Practice. Fundamentals, Methods, Experiments. 4 ed. Springer. Germany 2005. Ch. 2. Methods and Techniques for Synthesis, Characterization, Processing, and Modification of Polymers. (Year: 2005).*

(Continued)

*Primary Examiner* — Richard A Huhn
(74) *Attorney, Agent, or Firm* — Gordon & Jacobson, P.C.

(57) ABSTRACT

A method for preparing a copolymer that involves polymerizing at least one branched alkene monomer and at least one olefin monomer having a pendant benzocyclobutene (BCB) group to form a copolymer comprising a random distribution of a plurality of constitutional units corresponding to the at least one branched alkene monomer and the at least one olefin monomer. The polymerizing includes a carbocationic polymerization reaction involving sequential addition of a plurality of mixtures without terminating the carbocationic polymerization reaction, wherein the plurality of mixtures includes a mixture that includes the at least one branched alkene monomer and does not include the at least one olefin monomer having a pendant BCB group and a mixture that includes both the at least one branched alkene monomer and the at least one olefin monomer having a pendant BCB group. The copolymer composition can (Continued)

Proton NMR spectrum of Poly(st-co-4VBCB)-PIB-Poly(st-co-4VBCB) triblock copolymer.

undergo crosslinking at elevated temperatures (preferably above 180° C.).

18 Claims, 7 Drawing Sheets

Related U.S. Application Data of application No. 14/317,521, filed on Jun. 27, 2014, now Pat. No. 9,382,357, which is a continuation of application No. 12/145,704, filed on Jun. 25, 2008, now Pat. No. 8,765,895.

(60) Provisional application No. 60/986,384, filed on Nov. 8, 2007.

(51) Int. Cl.

| | | |
|---|---|---|
| *C08F 212/08* | (2006.01) | |
| *A61F 2/16* | (2006.01) | |
| *C08F 210/14* | (2006.01) | |
| *C08F 297/00* | (2006.01) | |
| *C08F 212/12* | (2006.01) | |
| *G02B 1/04* | (2006.01) | |
| *A61L 27/16* | (2006.01) | |
| *C08F 293/00* | (2006.01) | |
| *C08J 3/24* | (2006.01) | |
| *C08F 212/06* | (2006.01) | |

(52) U.S. Cl.
CPC .......... *C08F 210/14* (2013.01); *C08F 212/08* (2013.01); *C08F 212/12* (2013.01); *C08F 212/32* (2013.01); *C08F 293/00* (2013.01); *C08F 297/00* (2013.01); *C08J 3/247* (2013.01); *G02B 1/043* (2013.01); *A61F 2/1624* (2013.01); *A61F 2/1629* (2013.01); *A61F 2002/1681* (2013.01); *C08F 212/06* (2013.01); *C08J 2323/22* (2013.01); *C08J 2353/00* (2013.01)

(56) References Cited

U.S. PATENT DOCUMENTS

| | | | |
|---|---|---|---|
| 4,667,005 A | 5/1987 | Wong | |
| 4,687,815 A | 8/1987 | Wong | |
| 4,698,394 A * | 10/1987 | Wong ............... | C08F 212/04 525/289 |
| 4,946,899 A | 8/1990 | Kennedy et al. | |
| 5,422,410 A | 6/1995 | Tong et al. | |
| 5,451,647 A | 9/1995 | Faust et al. | |
| 5,516,610 A | 5/1996 | Nguyen et al. | |
| 5,741,331 A | 4/1998 | Pinchuk | |
| 5,990,033 A * | 11/1999 | Wilson ............... | C07F 17/00 502/103 |
| 6,102,939 A * | 8/2000 | Pinchuk ............ | A61L 27/16 600/36 |
| 6,197,240 B1 | 3/2001 | Pinchuk | |
| 6,268,451 B1 | 7/2001 | Faust et al. | |
| 6,512,056 B1 * | 1/2003 | Kennedy ............ | C08F 297/00 525/244 |
| 6,545,097 B2 | 4/2003 | Pinchuk et al. | |
| 6,780,954 B2 | 8/2004 | Lai et al. | |
| 6,855,770 B2 | 2/2005 | Pinchuk et al. | |
| 7,781,510 B2 | 8/2010 | Yalvac et al. | |
| 8,765,895 B2 * | 7/2014 | Zhou .................. | C08F 210/10 526/284 |
| 9,382,357 B2 * | 7/2016 | Zhou .................. | C08F 210/10 |
| 2004/0054103 A1 | 3/2004 | Webb et al. | |
| 2005/0187414 A1 | 8/2005 | Faust et al. | |
| 2006/0173145 A1 | 8/2006 | Pawlow et al. | |
| 2009/0124773 A1 * | 5/2009 | Zhou .................. | C08F 210/10 526/209 |
| 2016/0311952 A1 | 10/2016 | Zhou et al. | |

FOREIGN PATENT DOCUMENTS

| | | |
|---|---|---|
| WO | WO 2004/072133 | 8/2004 |
| WO | WO 2004/073018 | 8/2004 |

OTHER PUBLICATIONS

Benzocyclobutenes in Polymer Chemistry, M.F. Farona, Prog. Polym. Sci., vol. 21, 505-555, 1996.
Benzocyclobutenes in Polymer Synthesis, R.A. Kirchhoff et al, Prog. Polym. Sci., vol. 18, 85-185, 1993.
Caltronic Polymerizations—Mechanisms, Synthesis, and Applications, Matyjaszewski and Pugh, 1996, pp. 23-28, Dekker.
A Facile Approach to Architecturally Defined Nanoparticles via Intramolecular Chain Collapse, Harth et al, JACS Articles, Mar. 15, 2002.
"The First Example of Polymerization of Isobutylene induced by a Metallocene-like Initiator, [(eta-C5Me5)TiMe2[(mu-Me)B(C6F5)3]", Florin Barsan, Michael C. Baird, J. Chem. Soc., Chem. Commun., 1995, (10), 1065-1066.
Living carbocationic polymerization VIII. Telechelic polyisobutylenes by the MeO(CH2)2C-p-C5H4-C(CH3)2 Ome/ BCl3 initiating system. Mishra MK, Kennedy JP., Polym Bull 1987.
Living carbocationic polymerization XII. Telechelic polyisobutylenes by a sterically hindered bifunctional initiator. Wang B, Mishra MK, Kennedy JP., Polym Bull 1987;17:205.
A New, Non-Toxic, Curing Agent for Synthetic Polyolefins, Fishback et al, Bio-Medical Materials and Engineerin, vol. 2, pp. 83-87, 1992.
Polymer Synthesis: Theory and Practice, Fundamentals, Methods, Experiments, D. Braun et al., 4 ed. Springer, Germany 2005. Ch. 2.
Methods and Techniques for Synthesis Characterization, Processing and Modification of Polymers, p. 148-150.
Principles of Polymerization, ODIAN, 2004, pp. 506-510, 4th Edition, John Wiley & Sons.
Production of Crosslinked, Hollow Nanoparticles by Surface-Initiated Living Free-Radical Polymerization, Bloomberg et al, Journal of Polymer Science:Part A; Polymer Chemistry, vol. 40, 1309-1320 (2002).
Relative Reactivity of C4 Olefins toward the Polyisobutylene Cation, P. De and R. Faust, Macromolecules, vol. 39, pp. 6861-6870.
Solution Cross-Linked Poly(isobutylene) Gels: Synthesis and Swelling Behavior, Erman et al., Macromolecules, vol. 33, 2000 pp. 4822-4827.
Cationic Polymerization of 4-mttyl-1-pentene, Goodrich et al., Polymer Letters, 1964, 2, 353-357.

* cited by examiner

GPC results for synthesis of Poly(st-co-4VBCB)-PIB-Poly(st-co-4VBCB) triblock copolymer (Vial 1: starting PIB; vial 2: triblock)

Figure 2. Proton NMR spectrum of Poly(st-co-4VBCB)-PIB-Poly(st-co-4VBCB) triblock copolymer.

GPC RI traces of poly(IB-co-4VBCB) samples taken at various reaction times.

GPC UV traces of poly(IB-co-4VBCB) samples taken at various reaction times.

Figure 5. Proton NMR spectrum of poly(IB-co-4VBCB) (final product).

CROSSLINKED POLYOLEFINS FOR BIOMEDICAL APPLICATIONS AND METHOD OF MAKING SAME

CROSS-REFERENCE TO RELATED APPLICATIONS

This application is a continuation of U.S. application Ser. No. 15/202,239, filed Jul. 5, 2016, which is a continuation of U.S. application Ser. No. 14/317,521, filed Jun. 27, 2014, and issued as U.S. Pat. No. 9,382,357, on Jul. 5, 2016, which is a continuation of U.S. application Ser. No. 12/145,704, filed Jun. 25, 2008, and issued as U.S. Pat. No. 8,765,895, on Jul. 1, 2014, which claims benefit of U.S. provisional application Ser. No. 60/986,384, filed Nov. 8, 2007, all of which are hereby incorporated by reference herein in their entireties.

BACKGROUND OF THE INVENTION

1. Field

This invention relates to polymeric materials. The polymeric materials are particularly suitable for biomedical applications, such as a component of an intraocular lens.

2. State of the Art

Polymers have been used in biomedical applications for a long time. Early in vivo studies on polymeric implants revealed that the polymers are susceptible to degradation in physiological environment and lose integrity over time. A close scrutiny of the structure and bio-properties relationship led to Pinchuk's discovery of the superior biostability of polyisobutylene-based materials. The biomedical application of polyisobutylene-based materials is disclosed in U.S. Pat. Nos. 5,741,331; 6,102,939; 6,197,240; 6,545,097; and 6,855,770, all of which are herein incorporated by reference in their entirety. The first commercial application of such materials is the use of SIBS in the TAXUS® Stent of Boston Scientific Corporation, which is regarded as the most successful launch of a biomedical device in history.

SIBS is a thermoforming triblock copolymer consisting of polyisobutylene (PIB) as the rubbery center block and polystyrene (PS) as the hard side blocks. Due to the immiscibility of PIB and PS, the SIBS material has microphase-separated morphology in which PS phase forms physical crosslinks in the matrix of rubbery PIB phase. Due to the thermoplastic nature of the crosslinking, SIBS material creeps and can lose its dimension. SIBS doesn't withstand the high temperature of autoclave sterilization due to limitation by the glass transition temperature of PS. As a result, SIBS sterilization is difficult, because gamma-sterilization breaks down SIBS and ethylene oxide sterilization is cumbersome.

PIB is commonly crosslinked through vulcanization. First, isobutylene is copolymerized with a small fraction (1-5%) conjugated dienes such as butadiene, so that there are carbon-carbon double bonds in the backbone providing sites for vulcanization; second, the isobutylene/butadiene copolymer is heated with sulfur and crosslinked by the sulfur. To accelerate the vulcanization process, either the polymer is activated as in the case of halo-butyl rubber, or accelerators are added such as resins, zinc oxide, xanthates and quinoid systems. An extremely fast vulcanization process involves mixing butyl rubber solution with sulfur monochloride at room temperature (Erman et al, Macromolecules, Vol. 33, 2000, 4822-4827). The chemicals used for vulcanization of butyl rubber are toxic to human body. Extraction by solvent is necessary for removal of toxic residuals, but complete extraction is difficult and time-consuming.

PIB can be crosslinked utilizing silicone chemistry. Kaneka developed telechelic functional PIB (trade name: Epion) with silyl or allyl end groups, which can be crosslinked by moisture or adding silanes. Faust et al disclosed a virtually telechelic silyl PIB, which undergoes room temperature crosslinking as described in U.S. Pat. No. 6,268,451.

Benzocyclobutene derivates and 1-hexene were analyzed in Fishback et al., "A New Non-Toxic, Curing Agent for Synthetic Polyolefins," *Bio Medical Materials and Engineering*, Vol. 2, pp. 83-87 (1992), herein incorporated in reference in its entirety. Fishback prepared polymers containing 1-hexene, allyl-benzocyclobutene, and a diene, either 7-methyl-1,6-octadiene or 5-methyl-1,4-hexadiene, using free-radical polymerization techniques. While the polymer showed improved properties, it requires carbon black as a filler, and is polymerizable only through free-radical chemistry techniques that necessitate the use of free radical initiators. Additionally, there is a need to extract the non-crosslinked polymers to rid the system of the initiators as the initiators, if not removed, would leave the polymer with an undesirable purple color.

SUMMARY OF THE INVENTION

The present invention provides a polymeric composition including alkenes and benzocyclobutene-functional olefins that is polymerizable using living carbocationic chemistry.

The present invention provides such a polymeric composition that is biostable, exhibits increased tensile strength, and does not require a filler.

The present invention provides such a polymeric composition that is suitable for many applications.

The present invention provides such a polymeric composition that is crosslinked in a manner such that it has improved creep resistance and/or dimensional stability, especially when stressed or at elevated temperatures.

The present invention provides such a polymeric composition that does not release a small molecule to the environment.

The present invention provides such a polymeric composition that can withstand high temperature sterilization.

The present invention provides such a polymeric composition that is chemically crosslinked at elevated temperatures (e.g., greater than 180° C.) without addition or evolution of small molecules.

A copolymer composition of the present invention includes, in polymerized form, a branched alkene which is cationically polymerizable as well as a glass-forming comonomer and/or a vinyl comonomer containing benzocyclobutene (herein called "BCB") as the pendant group. The structure of the copolymer composition can take various forms: linear random copolymer, linear block copolymer, star random copolymer, star block copolymer, and other hyperbranched polymers and copolymers. The copolymer composition preferably undergoes crosslinking reaction at elevated temperatures (preferably above 180° C.).

It will be appreciated that the material of the present invention has improved structural characteristics and thus superior physical properties (such as creep resistance, heat resistance, dimensional stability and solvent resistance). By changing the copolymer composition and structure, materials with variable hardness and crosslinking density can be obtained for various biomedical applications. Examples of such uses include implantable medical devices such as synthetic heart valves, pharmaceutical closure devices, vertebral disks, joint menisci, artificial ligaments, artificial meniscuses, vascular grafts, pacemaker headers and lead insulators, glaucoma drainage tubes, intraocular lenses, and the like.

The material of the present invention also avoids the release of molecules that can cause inflammation when introduced in the body, which is characteristic of the silyl-terminated PIB of the prior art as it releases inflammation-introducing small molecules such as methanol, ethanol, acetic acid, chlorine and the like when cured.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
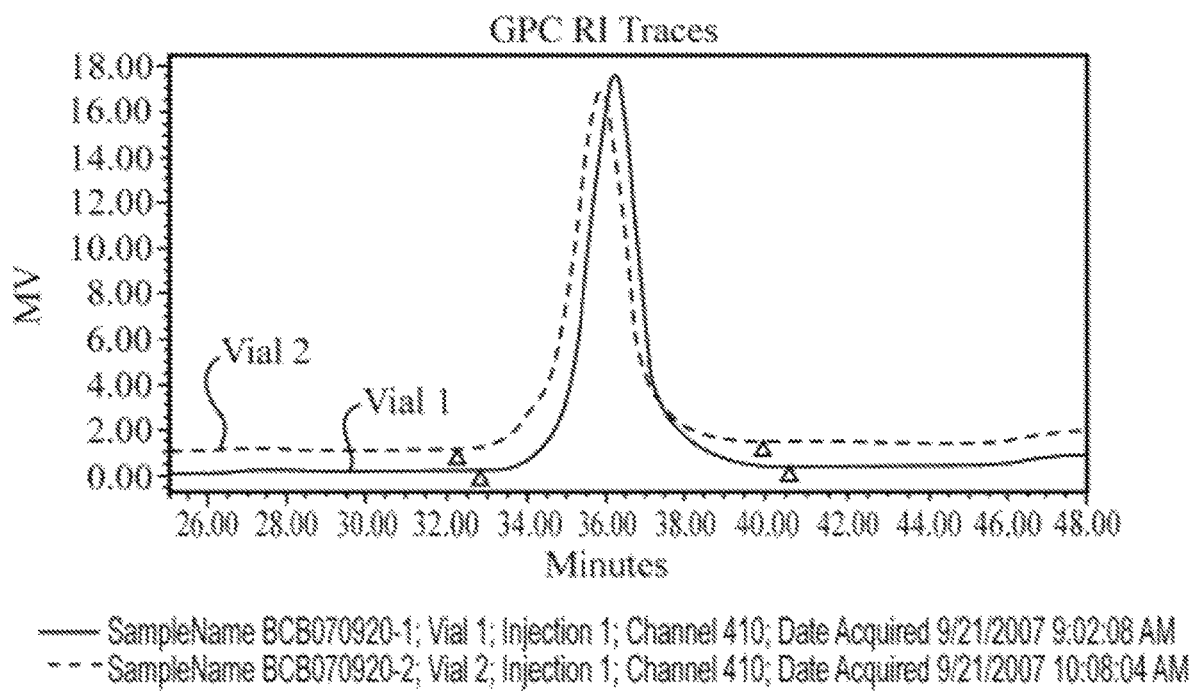
FIG. 1 is a graph Gel Permeation Chromatography (GPC) analysis of two samples, one sample being polyisobutylene and the other sample being Poly(st-co-4VCB)-PIB-Poly(st-co-4VCB).

In accordance with the present invention, a polymer composition suitable for biomedical applications includes copolymers comprising a plurality of constitutional units that correspond to one or more branched alkene monomer species as well as a plurality of constitutional units that correspond to one or more olefin monomer species with pendant BCB groups and/or a plurality of constitutional units that correspond to one or more glass-forming monomer species. Typically, each of these constitutional units occurs with the copolymer molecule at a frequency of at least 2 times, and more typically at least 50, 100, 1000 or more times. The copolymer composition preferably undergoes crosslinking reaction at elevated temperatures (preferably above 180° C.).

Due to the strained four-membered ring, benzocyclobutene (BCB) is converted to o-xylylene at temperatures above 180° C. At such elevated temperatures, the BCB group undergoes Diels-Alder reactions with dienophiles to form a six-membered ring, or reacts with itself to form an eight-membered ring. Polymers containing multiple pendant BCB groups per molecular chain can be thermally cross-linked with or without dienophiles. Each crosslink consists of a ring structure of carbon-carbon bond, which is more thermally stable than the sulfur bridge in vulcanized polymers and is stronger than the Si—O bond in silicone copolymers. The BCB crosslinking only involves heat. As long as the polymer is stable at the crosslinking temperature, there is no toxic chemical involved.

An embodiment of this invention relates to a polymer that comprises (a) a plurality of constitutional units that include at least one cationically polymerizable branched alkene monomer; (b) a plurality of constitutional units that include at least one cationically polymerizable olefin monomer having a pendant benzocyclobutene (BCB) group; and optionally (c) a plurality of constitutional units that include at least one glass-forming monomer, e.g., styrenic monomer or a non-reactive glassy compound. Preferably, the constitutional units of the glass-forming monomer are present in the polymer.

The branched alkene monomer may be any monomer that is both branched and contains a single double bond. The alkene should also be cationically polymerizable. Alkenes that are not cationically polymerizable, such as 1-hexene, cannot be added to the backbone of the polymer. Similarly, many dienes, such as 1,3-butadiene, cannot propagate in a cationic polymerization reaction, as the secondary carbon in the vinyl group will frequently cause the reaction to terminate. As such, dienes are typically only added to the backbone of a polymer as a cap or mono-addition to a living end. See De et al., "Relative Reactivity of C4 Olefins toward the Polyisobutylene Cation," Macromolecules, 39 (2006) pp. 6861-70. Additionally, effective cationic polymerization can be difficult using dienes having sterically hindered tertiary carbons.

Examples of suitable branched alkene monomers include $C_4$-$C_{14}$ branched alkenes such as isobutylene, 2-methyl-1-butene, 2-methyl-1-pentene, 2-methyl-1-hexene, and beta-pinene. Preferably, the alkene monomer is a small-chain alkene, such as a $C_4$-$C_7$ alkene. More preferably, the branched alkene monomer is an isoolefin, such as isobutylene, 2-methyl-1-butene, or 2-methyl-1-pentene.

The olefin monomer having a pendant BCB group may be any olefin monomer containing at least one BCB-functional moiety in the olefin. The olefin should be cationically polymerizable and compatible with the branched alkene. Suitable olefin monomers having a pendant BCB group include 4-vinylbenzocyclobutene, 4-(α-alkylvinyl)benzocyclobutenes such as 2-(4-benzocyclobutenyl)-propene and 2-(4-benzocyclobutenyl)-1-butene, and 4-(2-methyl-alkenyl)benzocyclobutenes such as 2-methyl-3-(4-benzocyclobutenyl)-1-propene and 2-methyl-4-(4-benzocyclobutenyl)-1-butene.

Preferred olefin monomers having a pendant BCB group have the formula

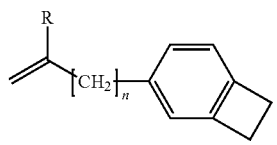

wherein R is hydrogen or an alkyl group (preferably methyl, ethyl, or propyl) and n is 0. Examples of this type of preferred olefin monomer include 4-vinylbenzocyclobutene and 2-(4-benzocyclobutenyl)-propene.

Preferred olefin monomers having a pendant BCB group also include compounds having the same formula

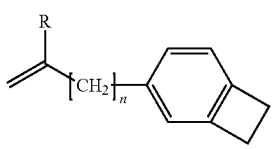

but wherein R is an alkyl group (preferably methyl, ethyl, or propyl) and n is an integer ranging from 1-3. Examples of this type of preferred olefin monomers include 2-methyl-3-(4-benzocyclobutenyl)-1-propene and 2-methyl-4-(4-benzocyclobutenyl)-1-butene.

As can be seen from the above formulas, which are identical, olefin monomers where n is 1-3 and R is hydrogen (for instance, allyl-benzocyclobutene) are not preferred, as these type of monomers are not cationically polymerizable.

Any glass-forming monomer known to those of skill in the art can be used in the polymer. Examples of suitable glass-forming monomers include styrenic monomers such as styrene, alpha-alkyl styrene (e.g., alpha-methyl styrene), 4-alkylstyrene, 4-alkoxystyrene, and various benzene-ring substituted styrenes. Suitable glass-forming monomers also include non-reactive glassy compounds such as norbornadiene or norbornene. The non-reactive glassy compounds are preferably bicyclic bridged systems that obey Bredt's rule, which states that the bridgeheads cannot be involved in a double bond. Compounds falling under this rule are typically inert. Preferably, the glass-forming monomer is styrene.

Additional olefins that are cationically polymerizable may also added to the polymer. For instance, the polymer may contain a plurality of constitutional units that include 1,3-dienes, vinyl ethers, N-vinyl ethers, N-vinyl carbazoles, N-vinyl pyrrolidone, aldehydes, ketones, or combinations thereof. An embodiment of this invention is directed towards a polymer in which the alkene component is copolymerized with one or more 1,3-dienes. Preferred 1,3-dienes include isoprene and 1,3-butadiene. Because the 1,3-dienes cannot be homopolymerized by cationic polymerization, it is preferable that they are copolymerized with isobutylene or another suitable branched alkene.

An embodiment of this invention also relates to a method of preparing a polymer, comprising the step of cationically polymerizing (a) at least one branched alkene monomer; (b) at least one olefin monomer having a pendant benzocyclobutene group; and optionally (c) at least one glass-forming monomer. In a preferred embodiment, the styrene is present.

The cationically polymerizable branched alkene monomer preferably contains a tertiary carbon on the vinyl group in the alkene. As known by those of skill in the art, cations are stable on the tertiary carbon due to the electron-donicity of the surrounding carbons that stabilize the positive charge of the cation. Polyisobutylene, a preferred branched alkene monomer, as discussed above, is an example of an alkene monomer polymerizable by cationic chemical means that contains a tertiary carbon. Molecules such as propene contain secondary carbons at the vinyl group and, as known by those of skill in the art, are not cationically polymerized.

Secondary carbons on the vinyl group after polymerization undesirably leave tertiary hydrogens that are easily extracted by simple oxidation means or even acid means to form double bonds. Therefore polymers of alkenes or olefins containing tertiary hydrogens, such as polypropylene and poly(1-hexene), tend to oxidize over time and become brittle. Consequently, alkenes having secondary carbons are not desirable for cationic polymerization reactions. On the other hand, alkenes containing tertiary carbons will form alternating quaternary carbons upon polymerizations. Polymers based upon these alternating quaternary carbons cannot support a double bond on its backbone; therefore, these polymers are much more stable over time and are better suited for uses such as implants, where the polymer should ideally be able to stay in the host for an extended period of time.

Like the branched alkene, the olefin monomer having a pendant benzocyclobutene (BCB) group should also be cationically polymerizable. A similar mechanism in the olefin monomer enables this. Olefins having a secondary carbon on the vinyl group are cationically polymerizable in instances when the electronegativity of the aromatic ring adjacent to the vinyl group can stabilize the cation. Thus olefins such as 4-vinylbenzocyclobutene, discussed above a preferred olefin, can be cationically polymerized. These type of olefins can be easily incorporated into the polymer simply by titrating it into the reaction during its polymerization. This is different than, for example, the allyl-BCB, which cannot be added to a cationic polymerization, in part because the aromatic ring in the BCB is not adjacent to the vinyl group.

Olefins having a pendant BCB and a tertiary carbon on the vinyl group are also suitable for cationic polymerization even if the vinyl group is not adjacent to the aromatic ring of the BCB. Tertiary carbons, which become quaternary carbons during polymerization, are stabilized by the electronegativity of the surrounding carbons. Therefore, olefins having tertiary carbons on the vinyl carbons can be incorporated into a cationic polymerized reaction much in the same manner as the alkene having a tertiary carbon is incorporated. 2-Methyl-3-(4-benzocyclobutenyl)-propene is an example of this type of compound. Also preferred are olefins that draw on the electronegativity of both the surrounding carbons and the aromatic ring, for example 2-(4-benzocyclobutenyl)-propene. These type of olefins will cationically polymerize as they are stabilized both by the methyl group (as in this case of 2-(4-benzocyclobutenyl)-propene) and the aromatic ring.

Method of preparing polymers via cationic polymerization are well known in the art. During the carbocationic polymerization process, the olefin having a pendent BCB group can be added at any time, that is, during the alkene addition, after the alkene polymerization is completed (with or without the glass-forming monomer), or both.

The copolymers of the present invention embrace a variety of configurations, for example, cyclic, linear and branched configurations. Branched configurations include star-shaped configurations (e.g., configurations in which three or more chains emanate from a single region), comb configurations (e.g., graft copolymers having a main chain and a plurality of side chains), and dendritic configurations (including arborescent or hyperbranched copolymers). The copolymers of the present invention embrace (a) copolymers comprising one or more chains containing repeating constitutional units of a single type (e.g., block copolymers), (b) copolymers comprising one or more chains containing randomly distributed constitutional units of two or more types (e.g., random copolymers), (c) copolymers comprising one or more chains containing two or more types of constitutional units that repeat within an ongoing series (e.g., alternating copolymers), such as triblocks, quadblocks, and so forth.

For example, in certain beneficial embodiments, the copolymers of the present invention are random copolymers containing (a) one or more alkene monomer units, which contain a plurality of units corresponding to one or more branched alkene monomer species and (b) one or more BCB-olefin monomer units, which contain a plurality of units corresponding to one or more BCB-olefin monomer species. Examples of branched alkene monomer species and BCB-olefin monomer species are discussed above.

For another example, in certain beneficial embodiments, the copolymers of the present invention are block copolymers containing (a) one or more olefin monomer blocks, which contain a plurality of units corresponding to one or more branched alkene monomer species and (b) one or more BCB-olefin monomer blocks, which contain a plurality of units corresponding to one or more BCB-olefin monomer species. Examples of branched alkene monomer species and BCB-olefin monomer species are discussed above. As above, in some embodiments, the BCB-olefin blocks can further contain a plurality of units that correspond to glass-forming monomer species.

The number average molecular weight (Mn) of the block copolymers of the present invention typically range, for example, from about 1000 to about 2,000,000, more typically from about 10,000 to about 300,000, even more typically 50,000 to 150,000, with the BCB-olefin units typically comprising 0.01-60 mol %, more typically 0.5-40 mol %, even more typically 0.5-5 mol % of the polymer. In some embodiments, polymers have a narrow molecular weight distribution such that the ratio of weight average molecular weight to number average molecular weight (Mw/Mn) (i.e., the polydispersity index) of the polymers ranges from about 1.0 to about 2.5, or even from about 1.0 to about 1.2.

Living polymerization, i.e., a polymerization that proceeds in the practical absence of chain transfer and termination, is a desirable objective in polymer synthesis. Living cationic polymerization implies that a polymer can be grown from one or from a plurality of active sites in a controlled manner (controlled molecular weight, molecular weight distribution, end functionalities, etc.). During this growth process, different molecules can be incorporated into the backbone of the polymer, yielding polymers with well-defined structures. For example, poly(styrene-block-isobutylene-block-styrene) ("SIBS") is a polymer where isobutylene is grown to a certain block size from two ends of a difunctional seed molecule and then styrene is infused into the reaction to cap the growing chain with glass-forming monomer segments. The result is a thermoplastic triblock polymer of polystyrene-polyisobutylene-polystyrene. One of the advantages of this type of polymer system is that depending upon the molar ratio of styrene to isobutylene, polymers can be made with durometers from Shore 20A to Shore 90D with a wide range of elongations. Another advantage of this triblock over a simple random polymerization of isobutylene and styrene is that the polymer blocks thus formed can segment into different domains which dramatically improve physical properties such as tensile strength, tear strength and compression set.

For certain other embodiments of the invention, when the copolymers of the present invention are random copolymer, conventional polymerization is employed in polymer synthesis. Random copolymers are formed by polymerizing monomer mixtures of (a) branched alkene monomer species (e.g., isobutylene) and (b) BCB-olefin monomer species (e.g., 4-vinylbenzocyclobutene or 2-(4-benzocyclobutenyl)-propene).

In some embodiments of the present invention, block copolymers are formed by the sequential monomer addition technique using (a) branched alkene monomer species (e.g., isobutylene) and (b) BCB-olefin monomer species (e.g., 4-vinylbenzocyclobutene or 2-(4-benzocyclobutenyl)-propene). As above, in some embodiments, a mixture of BCB-olefin and glass-forming monomer species may be used instead of BCB-olefin monomer species alone.

In one embodiment, the copolymers of the present invention are block copolymers containing (a) one or more olefin monomer blocks, which contain a plurality of units corresponding to one or more branched alkene monomer species, such as isobutylene, copolymerized with (b) one or more BCB-olefin monomer species, to produce a polymer comprised of polyisobutylene (or other polyalkene) dispersed with BCB crosslinkable units. In the presence of heat, for instance temperatures above 180° C., these polyisobutylene polymers containing BCB crosslinking units crosslink into 3-dimentional thermoset materials.

In another embodiment, the copolymers described above containing polyisobutylene co-polymerized with BCB can be mixed in the melt (below 180° C.) with other copolymers. The other copolymer may be, for instance, block copolymers containing (a) one or more glass-forming monomer blocks, which contain a plurality of units corresponding to one or more glass-forming monomer species, such as alpha-methyl styrene, copolymerized with (b) one or more BCB-olefin monomer species to produce a copolymer comprised of poly(alpha-methyl styrene) (or other glass-forming monomer) dispersed with BCB crosslinkable units. In the presence of heat, for instance temperatures above 180° C., these polyisobutylene polymers containing BCB crosslinkable units can crosslink to the poly(alpha-methyl styrene) polymers containing BCB crosslinkable units to form 3-dimentional thermoset materials that, depending upon the ratios of the above copolymers, can provide rubbery to stiff materials with exceptional physical and chemical properties.

In many embodiments, the polymer is formed at low temperature from a reaction mixture that comprises: (a) a solvent system appropriate for cationic polymerization, (b) one or more branched alkene monomer species, (c) an initiator, and (d) a Lewis acid coinitiator. In addition, a proton-scavenger is also typically provided to ensure the practical absence of protic impurities, such as water, which can lead to polymeric contaminants in the final product. An inert nitrogen or argon atmosphere is generally required for the polymerization.

Polymerization can be conducted, for example, within a temperature range of from about 0° C. to about −100° C., more typically from about −50° C. to −90° C. Polymerization times are typically those times that are sufficient to reach the desired conversion.

Among the solvent systems appropriate for cationic polymerization, many of which are well known in the art, are included: (a) $C_1$-$C_4$ halogenated hydrocarbons, such as methyl chloride and methylene dichloride, (b) $C_5$-$C_8$ aliphatic hydrocarbons, such as pentane, hexane, and heptane, (c) $C_5$-$C_{10}$ cyclic hydrocarbons, such as cyclohexane and methyl cyclohexane, and (d) mixtures thereof. For example, in some beneficial embodiments, the solvent system contains a mixture of a polar solvent, such as methyl chloride, methylene chloride and the like, and a nonpolar solvent, such as hexane, cyclohexane or methylcyclohexane and the like.

Initiators for living carbocationic polymerization are commonly organic ethers, organic esters, organic alcohols, or organic halides, including tert-ester, tert-ether, tert-hydroxyl and tert-halogen containing compounds. Specific examples include alkyl cumyl ethers, cumyl halides, alkyl cumyl esters, cumyl hydroxyl compounds and hindered versions of the same, for instance, dicumyl chloride, 5-tert-butyl,1,3-dicumyl chloride, and 5-tert-butyl-1,3-bis(1-methoxy-1-methylethyl)benzene. 5-tert-butyl-1,3-bis(1-methoxy-1-methylethyl)benzene is the preferred initiator for cationic polymerization and may be prepared through the methods disclosed in Wang B. et al., "Living carbocationic polymerization XII. Telechelic polyisobutylenes by a sterically hindered bifunctional initiator" Polym. Bull. (1987) 17:205-11; or Mishra M. K., et al., "Living carbocationic polymerization VIII. Telechelic polyisobutylenes by the $MeO(CH_2)_2C$-p-$C_5H_4$—$C(CH_3)_2$ $OMe/BCl_3$ initiating system" Polym. Bull. (1987) 17:7-13, both of which are herein incorporated by reference in their entirety. The initiators used for crosslinkable polyolefins described in this invention include mono or multifunctional initiators.

Carbocationically terminated star polymers can be formed by selecting initiators having three or more initiation sites, for example, tricumyl chloride (i.e., 1,3,5-tris(1-chloroy-1-methylethyl)benzene), which contains three initiation sites.

Examples of Lewis acid coinitiators include metal halides such as boron trichloride, titanium tetrachloride and alkyl aluminum halides. The Lewis acid coinitiator is typically used in concentrations equal to or greater, e.g., 2 to 50 times greater, than the concentration of the initiator.

Examples of proton-scavengers (also referred to as proton traps) include substituted or unsubstituted 2,6-di-tert-butylpyridines, such as 2,6-di-tert-butylpyridine and 4-methyl-2,6-di-tert-butylpyridine, as well as 1,8-bis(dimethylamino)-naphthalene and diisopropylethyl amine. The concentration of the proton trap is preferably only slightly higher than the concentration of protic impurities such as water in the polymerization system.

Further information regarding the preparation of block copolymers from monomer species that have significantly different reactivities can be found, for example, in United States Patent Application No. 20050187414, herein incorporated by reference in its entirety.

A beneficial aspect of this invention is that the polymers make excellent thermoplastics. The resultant thermoplastic polymer can be cleaned by multiple dissolution and precipitation procedures, which can be especially useful in medical applications, as it is still soluble in solvents. In addition, the polymer can then be molded or extruded or cast into its desired shape and then heat cured to react the olefin having the pendant BCB group with itself to crosslink the polymer into a thermoset shape. The resultant product provides better heat stability, better creep resistance, less water uptake, and less swelling or solubility in organic solvents. Another advantage of a thermoset polymer is that the polymer can be heat or solvent compounded with plasticizers including polyisobutylene, mineral oil, paraffin oil and the like to soften the polymer.

Once crosslinked, the polymer can be used for heart valves, vertebral disks, dynamic stabilizers, sealable vascular grafts, stent grafts, intraocular lens (e.g., accommodating intraocular lenses), glaucoma drainage implants, pacemaker headers, pacemaker lead insulators and other implantable medical devices as well as other medical devices where exceptional compression set or creep resistance are important. Additionally, the polymers have use for various uses outside the biomedical field, such use as O-rings or as components of windshield wipers.

The invention is further described with reference to the following non-limiting examples.

Example 1: Synthesis of poly(st-co-4VBCB)-polyIB-poly(st-co-4VBCB) Triblock Copolymer 337 mL of methylcyclohexane (MeCHx) were added to a glass reaction vessel equipped with mechanical stirrer, stainless steel serpentine tubing for liquid nitrogen cooling, stainless steel tubing for feeding methyl chloride (MeCl) and isobutylene (IB) into the vessel, a thermocouple with temperature controller, a nitrogen bubbler and an addition dropping funnel. The liquid was cooled down to −80° C. by liquid nitrogen cooling. Sequentially MeCl (189 g) and IB (20 g) were added through the feeding line immersed in the liquid, so that the gases are condensed into the liquid. While gases were being condensed, an initiator solution (HDCE/DTBP/MeCHx 0.28 g/0.45 mL/15 mL) was added through a port on the reactor lid. $TiCl_4$ (3.5 mL, use a 10 cc glass syringe) was then added through an opening in the reactor lid, which started the IB polymerization (the timer is started). Forty minutes later, ~4 mL of reaction mixture was withdrawn from the reactor and quenched in excess methanol. A mixture of styrene/4VBCB/MeCHx (7 mL/2 mL/20 mL) was added slowly into the reactor through a syringe in 2 minutes. After 6 minutes, the reaction was quenched with excess methanol. As is well known in the art, the term "HDCE" refers to 5-Tert-butyl-1,3-bis(1-methoxy-1-methylethyl)-benzene, also called 5-tert-butyl-1,3-dicumyl ether, aka hindered dicumyl ether (HDCE), and the term "DTBP" refers to 2,6-di-tert-butyl-pyridine.

The reaction mixture was stored under the fume hood overnight. The top layer was separated and washed repeatedly with distilled water until neutral. The solution was precipitated into isopropyl alcohol, followed by dissolution in toluene and precipitation in isopropyl alcohol again. The precipitate was dried in a vacuum oven at ~60° C. until constant weight (yield: 22 g).

Figure 2:
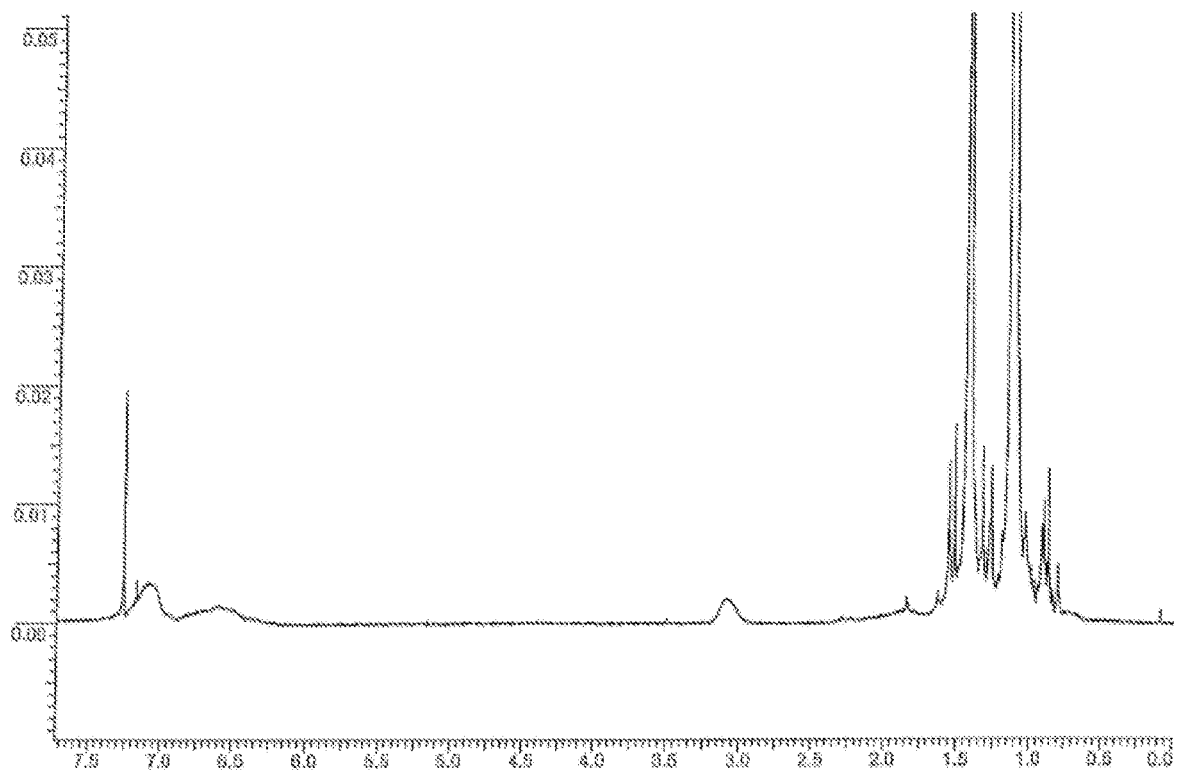
FIG. 2 is a spectrum of NMR analysis of the Poly(st-co-4VCB)-PIB-Poly(st-co-4VCB) sample of FIG. 1.

The polymer was characterized by GPC and NMR. As shown in FIG. 1, both the starting PIB (low elution volume) and the triblock copolymer (high elution volume) show a narrow monodispersed peak in GPC RI traces, and the traces shift smoothly as molecular weight increases. As shown in FIG. 2, there is a singlet at ~3.1 ppm in proton NMR spectrum, which is attributed to the strained ring of BCB. The broad peaks at ~6.4-7.3 ppm are attributed to aromatic protons on styrene and 4-VBCB monomer units. From the relative integration intensities, the copolymer was determined to have ~3 mol % 4-VBCB and ~7 mol % styrene.

Example 2: Synthesis of poly(IB-co-4VBCB) Random Copolymer 337 mL of methylcyclohexane (MeCHx) were added to a glass reaction vessel equipped with mechanical stirrer, stainless steel tubing for liquid nitrogen cooling, stainless steel tubing for feeding methyl chloride (MeCl) and isobutylene (IB) into the vessel, a thermocouple with temperature controller, a nitrogen bubbler and an addition dropping funnel. The liquid was cooled down to −80° C. by liquid nitrogen cooling. Sequentially MeCl (189 g) and IB (5 g) were added through the feeding line immersed in the liquid, so that the gases are condensed into the liquid. While gases are being condensed, an initiator solution (HDCE/DTBP/MeCHx 0.28 g/0.45 mL/15 mL) was added through a port on the reactor lid. $TiCl_4$ (3.5 mL, using a 10 cc glass syringe) was then added through an opening in the reactor lid, which starts the IB polymerization (the timer was started). Five minutes later, 36 g of IB and 1.5 g 4VBCB (dissolved in 10 mL of MeCHx) were added slowly, taking 7 min and 9.5 min, respectively. After all 4-VBCB was added, the reaction is kept going for 60 min. Samples were taken at 5, 30 and 60 min. The reaction was quenched with excess methanol in the end.

The reaction mixture was stored under the fume hood overnight. The top layer was separated and washed repeatedly with distilled water until neutral. The solution was precipitated into isopropyl alcohol, followed by dissolution in hexane and precipitation in isopropyl alcohol again. The precipitate was dried in a vacuum oven at ~60° C. until constant weight (yield: 35 g).

Figure 3:
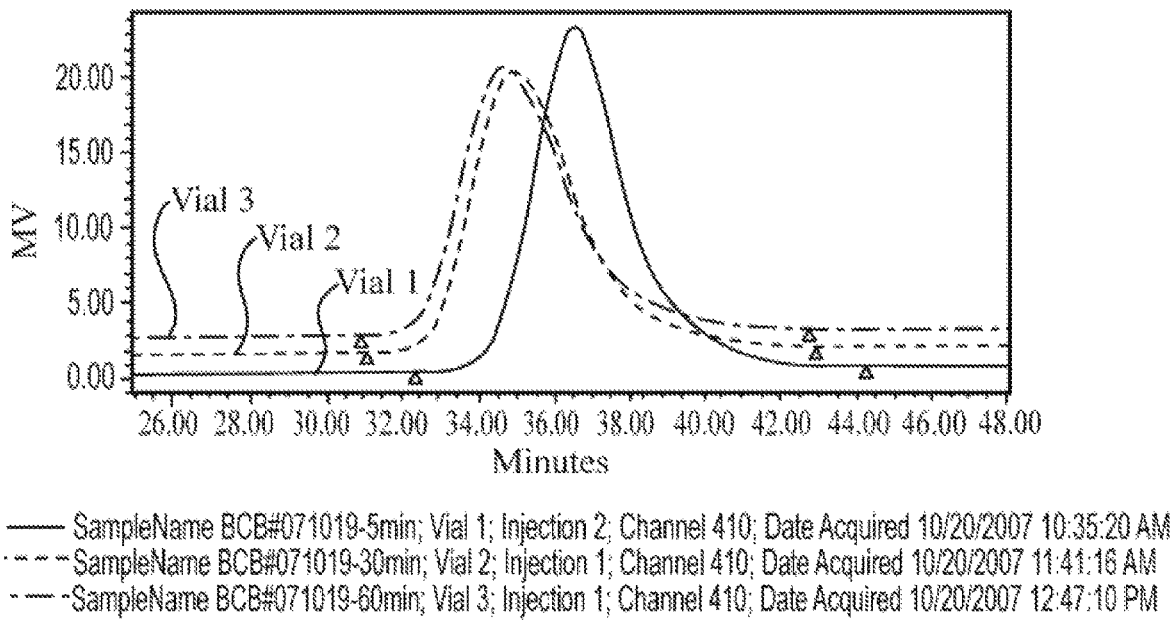
FIG. 3 is a graph GPC RI analysis of three samples of Poly(IB-co-4VCB) at various reaction times.
Figure 4:
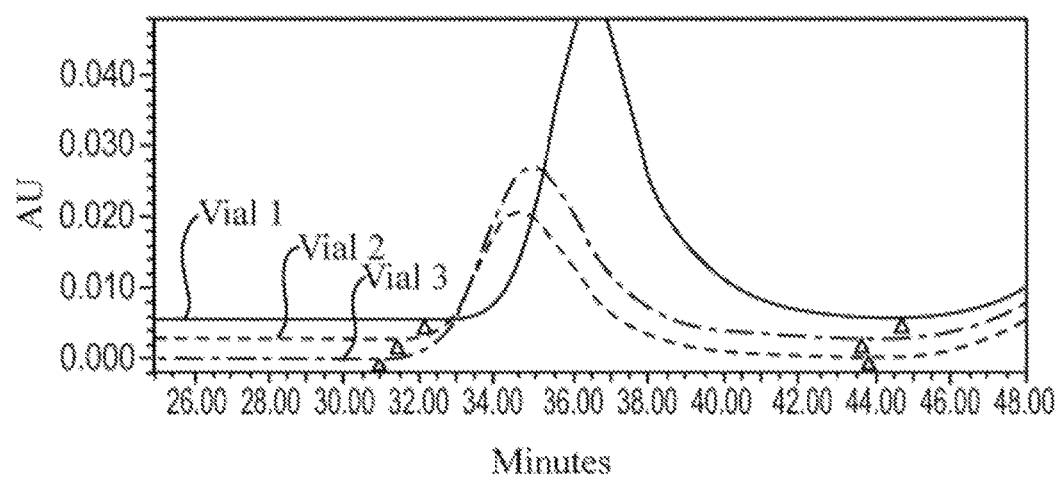
FIG. 4 is a GPC UV analysis of the Poly(IB-co-4VCB) samples of FIG. 3.
Figure 5:
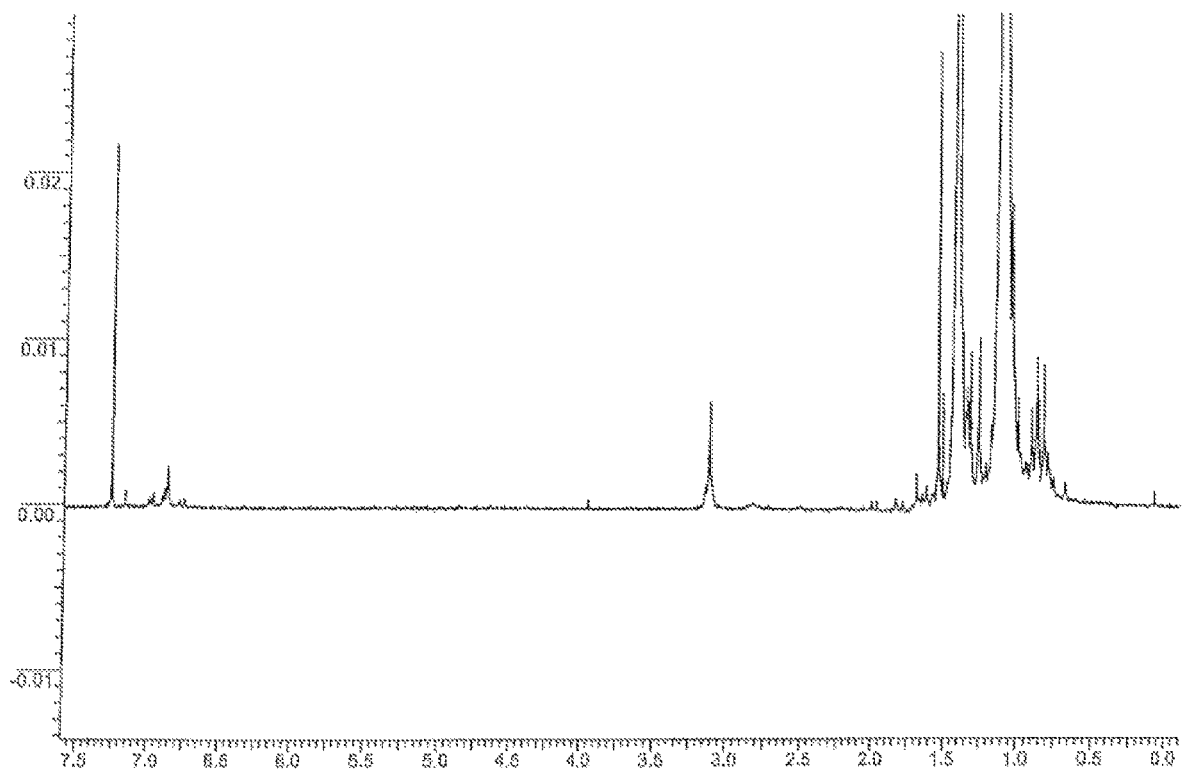
FIG. 5 is a spectrum of NMR analysis of a Poly(IB-co-4VCB) sample synthesized in accordance with the present invention.

The polymer was characterized by GPC and proton NMR. GPC RI traces of the samples show (see FIG. 3) that the molecular weight increases with reaction time. Little change was observed in molecular weight (~10%) from 30 min to 60 min, as the polymerization approached completion. Each sample had a UV signal with similar elution volume as its RI signal (FIG. 3, 4). The sample taken at 5 min exhibited a much stronger UV signal than the other two, indicating that it has a higher 4-VBCB content at lower conversion. The incorporation of 4-VBCB into the copolymer was further confirmed by proton NMR spectroscopy. A singlet at ~3.1 ppm was seen in proton NMR spectrum (FIG. 5), which is attributed to the strained ring of BCB.

When heated up to 240° C. for 10 min, the copolymer became insoluble in THF and thus thermally crosslinked.

Example 3: Thermal Crosslinking of poly(st-co-4VBCB)-polyIB-poly(st-co-4VBCB) Triblock Copolymer A sample (0.2 g) of the poly(st-co-4VBCB)-polyIB-poly(st-co-4VBCB) triblock copolymer as formed above was placed between two Teflon films, and the films placed between two flat metal plates. The resulting structure was placed in a hot press (250° C.) for 10 minutes with virtually no pressure applied. The Teflon films were removed from the plates and cooled to room temperature. A small piece of the heat treated polymer was placed in a vial containing THF. The film remained insoluble overnight and longer, indicating that it crosslinked.

Polymer samples were thermally treated at different temperatures for 10 minutes. At temperatures above 220° C., the resultant polymer is insoluble in THF. At a temperature of 200° C., the resultant polymer is soluble in THF. For thermal crosslinking below 220° C., extended time period (>10 min) may be necessary.

Example 4: Preparation of a SIBS Triblock Polymer

SIBS was prepared in two steps in one pot. In the first step, isobutylene was polymerized by a 5-tert-butyl,1,3-dicumyl chloride/TiCl$_4$ initiating system in a methyl chloride/hexanes solvent system in the presence of a proton trap under a blanket of dry nitrogen at –80° C. When the central PIB block reached the desired molecular weight, in this case 50 KDaltons, a sample was removed from the reactor and styrene was added to the reactor and the polymerization continued until the outer polystyrene blocks also reach a predetermined length, in this case 75 KDaltons. The process was terminated by the addition of methanol. The sample that was taken was dried in an oven. After drying in the oven, the sample was observed to have a consistency similar to that of a rubber band.

Example 5: Comparative Example Using 1-Hexene

This experiment was run to compare the effect of polyisobutylene, as described in Example 4, with 1-hexene. 1-hexene was dissolved in a methyl chloride/hexanes solvent system and the mixture was added to the reaction pot in the presence of a 5-tert-butyl,1,3-dicumyl chloride/TiCl$_4$ initiating system, also in a methyl chloride/hexanes solvent system, in the presence of a proton trap under a blanket of dry nitrogen at –80° C. However, in this case, at the end of the addition, a sample was taken which when dry, resembled a lumpy oil. The reaction never went to completion because to chain termination effects. The styrene was never added to the reactor as the experiment was aborted.

Based on these results, it was concluded that 1-hexene could not achieve an elastomer by cationic polymerization. Instead, the reaction produced low molecular weight oils.

In accordance with another aspect of the invention, the polymeric material as described herein realizes an intraocular lens (IOL) for the replacement of the natural crystalline lens of the eye. The natural crystalline lens is a gel-like material that sits within the lens capsule of the eye and when the lens capsule is stretched by the zonules, the gel changes its thickness and therefore its focal point thereby allowing focusing at different distances. When the natural lens is removed from the lens capsule, lens epithelial cells (LECs) begin to multiply and spread on the posterior wall of the lens capsule and effectively render the posterior wall opaque (referred to as "posterior capsule opacification" or PCO), which results in impaired vision. The LEC's also spread on the anterior wall. However, due to the opening in the anterior wall of the lens capsule (the capsulorrhexus) employed in traditional IOL implantations, there is no wall for them to spread onto. The occurrence of PCO is relatively high in traditional IOL implantations where the LECs spread between the IOL and the lens capsule.

In the preferred embodiment, the polymeric material as described herein is used to form a one-piece IOL that includes an optic portion with an outer peripheral edge as well as one or more haptic elements (or haptics) that project radially outward from the peripheral edge of optic portion as shown in FIGS. 6-8C.

Figure 6:
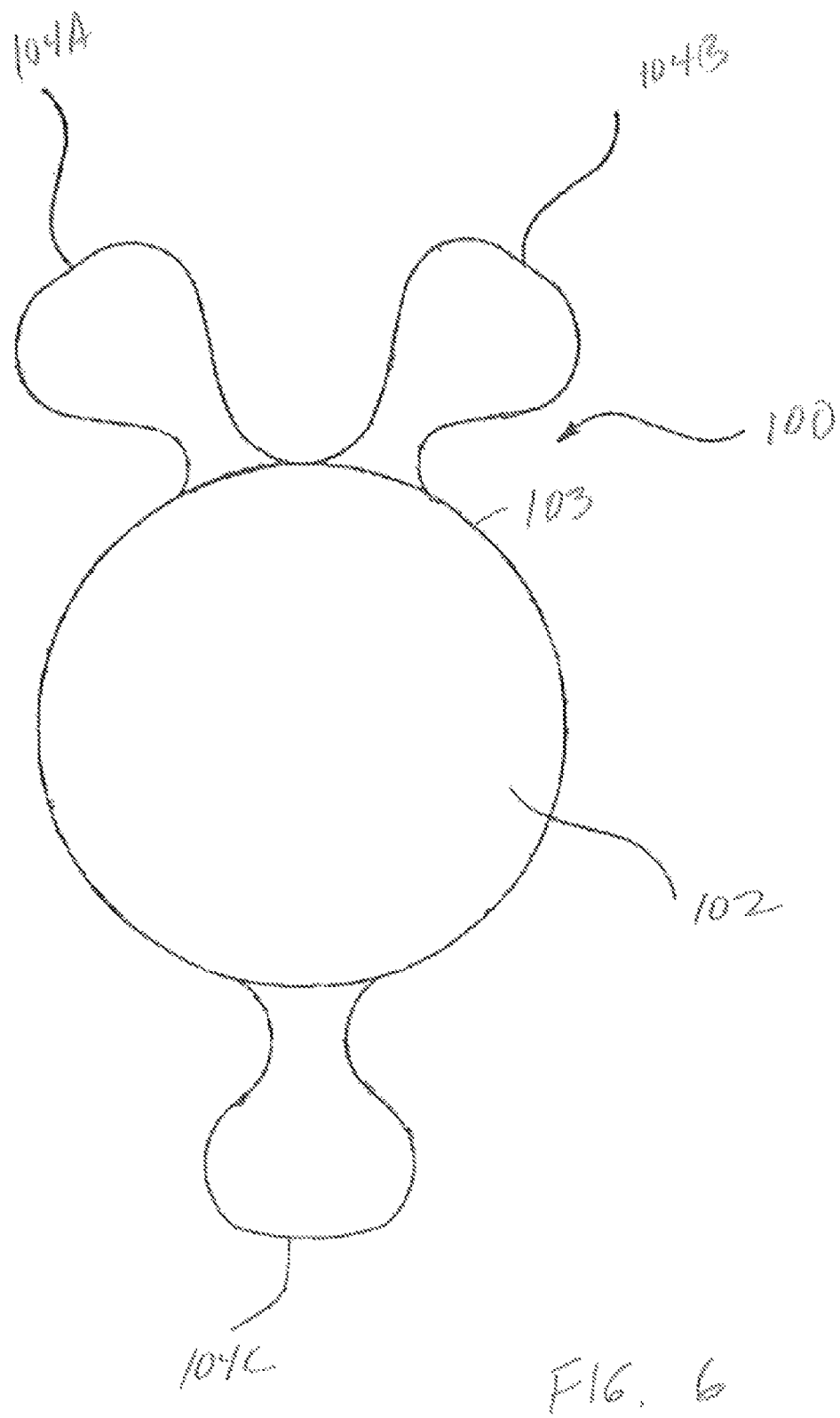
FIG. 6 is a front view of an exemplary embodiment of an intraocular lens device in accordance with the present invention.

In the embodiment of FIG. 6, the IOL 100 includes an optic portion 102 with an outer peripheral edge 103. Three haptic elements 104A, 104B, 104C (collectively, 104) project radially outward from the peripheral edge 103 of optic portion 102. The haptic elements 104 are preferably integrally formed with and permanently connected to the outer peripheral edge 103 of optic portion 102. Different haptic designs, such as those that utilize two haptics or four haptics can also be used.

Figure 7:
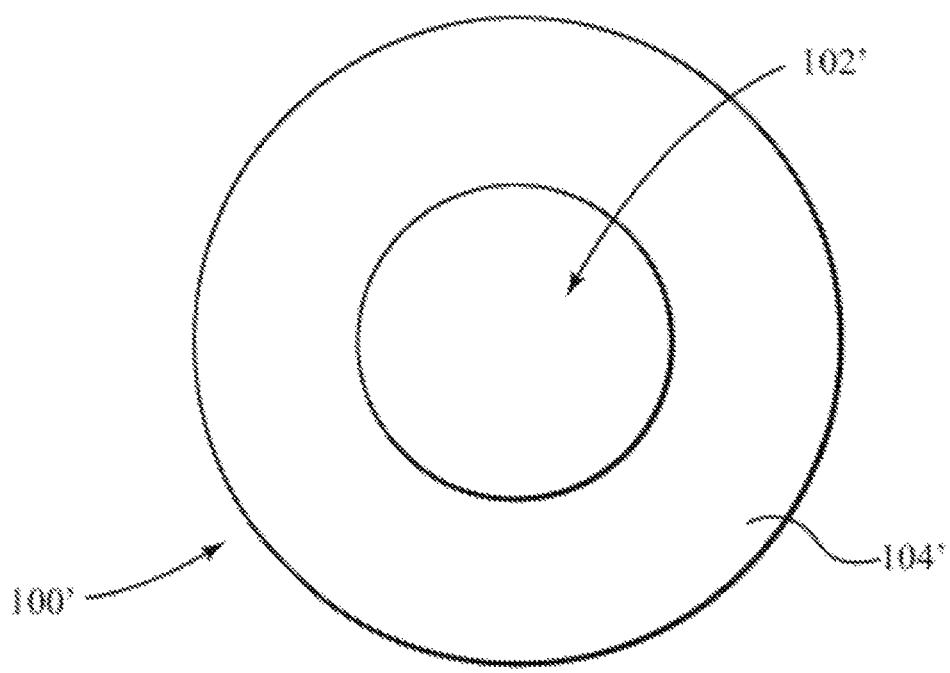
FIG. 7 is a front view of an alternate embodiment of an intraocular lens device in accordance with the present invention.
Figure 8A:
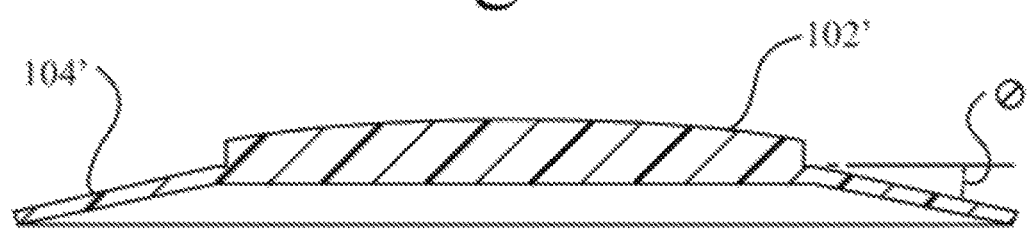
FIGS. 8A, 8B and 8C illustrate different annular haptic designs that can be utilized in the embodiment of FIG. 6.
Figure 8B:
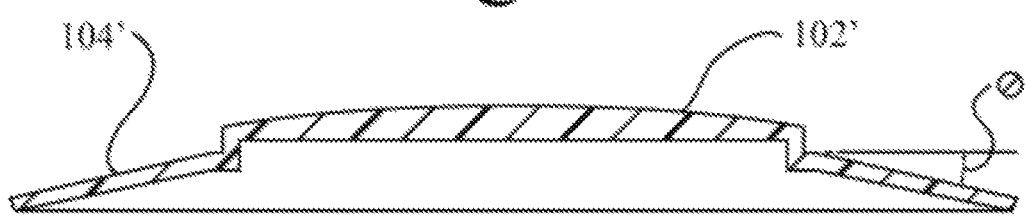
Figure 8C:
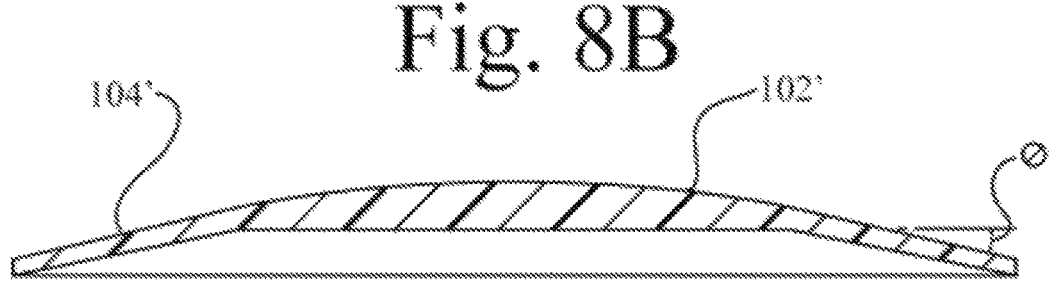

In the embodiment of FIGS. 7-8A, the IOL 100' employs a ring haptic 104' as is well known in the art. FIG. 7 illustrates a top view of the IOL 100' with an optic portion 102" and a ring haptic 104'. Cross-sections for different embodiments are shown in FIGS. 8A-8C. The front and back surfaces of optic portion 102' can be of any diopter (curvature) necessary to provide the desired correction for the patient. For example, the front surface of the optic portion 104' may be convex as shown in FIG. 8A-8C or possibly concave (not shown). The back surface of the optic portion 104' is preferably flat as shown in FIGS. 8A-8C, but it may be concave or convex to add or subtract magnification. As shown in FIGS. 8A-C, the angle θ of the annulus of the ring haptic 104' relative to the plane of the optic portion 104' (which is disposed substantially perpendicular to the optical axis of the eye) is between 0 and 45 degrees, and more preferably between 10 and 20 degrees, and most preferably 15 degrees.

The terminal end(s) of the haptic(s) of the IOL as described herein are adapted to rest in and engage the lens capsule where such terminal end(s) is(are) held in place through compressive forces exerted by the inner surfaces of the lens capsule. The haptic(s) preferably do not lie in the plane of the optic portion but are angled relative to the optic portion (for example, at 15 degrees) such that posterior side of the optics portion presses against and contacts the posterior wall of the lens capsule. This configuration (which is typically referred to as a "vaulted configuration" or "vaulted haptics") is important because the pressure of the optics portion against the posterior wall of the lens capsule prevents epithelial cells from migrating between the optics portion and the posterior wall and thereby mitigates the occurrence of PCO. Moreover, due to the crosslinked nature of the polymeric material as described herein, the vaulted haptics realized from such polymeric material maintain pressure of the optics portion against the posterior wall of the lens capsule over time and thus mitigates the occurrence of PCO over time.

In addition, when accommodation is desired, the haptics of the IOL act as a hinge which allows the optics portion to move forward or backwards along the optical axis of the eye. The crosslinked nature of the polymeric material as described herein allows for such hinged movement while providing memory that returns the haptics to their original shape during such accommodation. Moreover, the polymeric material as described herein better resists fatigue under the flex stresses imposed during accommodation as compared to the acrylic lenses currently on the market. More specifically, acrylic lenses are not used for accommodating IOLs for this reason. Typically, silicone is used for accommodating IOLs, but silicone IOLs are thick. In addition, silicone swells when silicone oil is used following victrectomy; that is when the vitreous humor is removed and replaced with silicone oil, the silicone IOL will swell. Silicone oil has no effect on an IOL realized from the polymeric material as described herein.

The polymeric material as described herein provides an index of refraction in the range between 1.525 and 1.535 as compared to an index of refraction between 1.25 and 1.42 for silicone rubber. This higher index of refraction provides greater magnification as compared to silicone rubber, which enables the IOL realized from the polymeric material described herein to be thinner than silicone rubber IOLs. A thin IOL is advantageous as it can be introduced into lens capsule through a smaller size cannula and thus reduces the size of the surgical incision into the lens capsule. The reduced size incision lessens the chance of an astigmatism that can possibly result therefrom when the incision is sutured closed. Moreover, it is contemplated that the thin IOL can be deployed into the lens capsule through an incision less than 2.5 mm. In this case, a suture is not necessary to close the incision and astigmatisms are not a concern.

In the preferred embodiment, the polymeric material of the IOL includes PIB crosslinked by at least one BCB-olefin monomer as described herein due to the homogeneity of such material. It is also contemplated that the polymeric material of the IOL can be made gel like to form a phako-ersatz lens. In this embodiment, the polymeric material as described herein can be made into a gel for realizing the IOL by blending in, either with heat or in solvent, plasticizers such as low molecular weight PIB, mineral oil, paraffin oil, organic solvents (toluene, hexane, heptane, octane, nonane, decane, dodecane, etc.) or any other aliphatic plasticizer. For example, at 90% plasticizer, the polymeric material as described herein becomes jell-o-like.

When PIB is used as part of the polymeric material of the IOL, the PIB is typically synthesized in organic solvent using a Lewis acid as an initiator. One such Lewis acid that is preferred for this application is titanium tetrachloride. In order to quench the reaction, chemicals such as alcohols (methanol, for example) are added in excess to the reaction stoichiometry which immediately quenches the reaction by neutralizing titanium tetrachloride. At completion of the reaction, titanium tetrachloride is converted into various salts of titanium, including titanium dioxide, titanium methoxide, and the like. In addition, depending upon the reaction vessel used, various salts of titanium can form with materials inherent to the reaction vessel, especially if the vessel is comprised of stainless steel—these salts render the material black with time. Nevertheless, a consequence of adding these reactant materials is that in order to render the material clean and highly transparent, these excess materials and their byproducts must be removed from the polymer upon completion of the reaction. These remnant salts and other unwanted chemicals are preferably washed from the PIB material by washing the polymer in a separatory funnel with salt water, with pure water and with repeated precipitations in excess polar solvent (such as isopropanol, acetone, methanol, ethanol and the like). Other well-known washing procedures can also be used. Note that if the material is not washed of salts, these hygroscopic salts begin to draw in water when the material is equilibrated in water. Voids where the salts have been trapped are readily viewed under scanning electron microscopy and these voids become filled with water as the salt is dissolved out. As water has a refractive index of approximately 1.33 and material has a refractive index of 1.53, the difference in refractive index is sufficient to render the polymer cloudy and at times totally opaque. If the material is washed appropriately, these salts are removed and voids no longer exist.

When used as an IOL, the polymer can be compounded with radiopaque fillers and the like to enable visualization under X-ray or angiography. Other fillers and additives known in the art of preparing an IOL can also be added using known techniques and procedures.

There have been described and illustrated herein several embodiments of polymers and crosslinked polyolefins for biomedical applications as well as methods of making same. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed.

What is claimed is:

1. A method of preparing a copolymer comprising:
polymerizing at least one branched alkene monomer and at least one olefin monomer having a pendant benzocyclobutene (BCB) group to form a copolymer comprising a random distribution of a plurality of constitutional units that include constitutional units corresponding to the at least one branched alkene monomer and constitutional units corresponding to the at least one olefin monomer having a pendant BCB group;

wherein the polymerizing includes a carbocationic polymerization reaction involving i) forming a mixture that includes the at least one branched alkene monomer and at least one initiator compound to initiate a polymerization reaction of the at least one branched alkene monomer, wherein the mixture does not include the at least one olefin monomer having a pendant BCB group, and ii) adding both the at least one branched alkene monomer and the at least one olefin monomer having a pendant BCB group to the polymerization reaction of i) without terminating the carbocationic polymerization reaction.

2. A method according to claim 1, wherein:
the first mixture further includes at least one solvent.

3. A method according to claim 1, wherein:
the at least one branched alkene monomer comprises an isoolefin selected from the group consisting of isobutylene, 2-methyl-1-butene, 2-methyl-1-pentene, 2-methyl-1-hexene, and combinations thereof.

4. A method according to claim 1, wherein:
the at least one branched alkene monomer comprises isobutylene.

5. A method according to claim 1, wherein:
the at least one initiator compound of the mixture includes a Lewis acid coinitiator and an initiator selected from the group consisting of: a) organic ethers, b) organic esters, c) organic alcohols, d) organic halides, including tert-ester, tert-ether, tert-hydroxyl and tert-halogen containing compounds, e) alkyl cumyl ethers, cumyl halides, alkyl cumyl esters, cumyl hydroxyl compounds and hindered versions of the same, f) dicumyl chloride, g) 5-tert-butyl-1,3-bis(1-methoxy-1-methylethyl)benzene (HDCE), h) initiators having three or more initiation sites, and i) tricumyl chloride.

6. A method according to claim 1, wherein:
the at least one initiator compound of the mixture includes a Lewis acid and 5-tert-butyl-1,3-bis(1-methoxy-1-methylethyl)benzene (HDCE).

7. A method according to claim 1, wherein:
the at least one olefin monomer having a pendant BCB group comprises a monomer having the formula

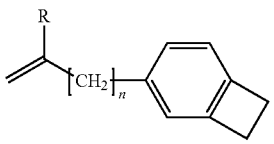

wherein R is hydrogen or an alkyl group and n is 0.

8. A method according to claim 7, wherein:
the at least one olefin monomer having a pendant BCB group comprises 4-vinylbenzocyclobutene or 2-(4-benzocyclobutenyl)-propene.

9. A method according to claim 1, wherein:
the at least one olefin monomer having a pendant BCB group comprises a monomer having the formula

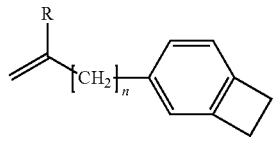

wherein R is alkyl group and n is an integer ranging from 0-3.

10. A method according to claim 9, wherein:
the at least one olefin monomer having a pendant BCB group comprises 2-methyl-3-(4-benzocyclobutenyl)-propene.

11. A method according to claim 1, wherein:
the copolymer further includes a glass-forming monomer selected from the group consisting of styrene, indene, α-methylstyrene, p-tert-butylstyrene, p-chlorostyrene, norbornene, and combinations thereof.

12. A method according to claim 11, wherein:
the glass-forming monomer is styrene.

13. A method according to claim 1, wherein:
the at least one olefin monomer having a pendant BCB group is present in amount ranging from 0.01 to 60 mol % of the monomeric units of the copolymer.

14. A method according to claim 1, wherein:
the carbocationic polymerization reaction is a living cationic polymerization reaction.

15. A method according to claim 1, wherein:
the copolymer undergoes crosslinking when exposed to temperatures of at least 180° C.

16. A method of preparing a thermoset polymer comprising:
processing a copolymer prepared according to claim 1 to form a resultant thermoset polymer, wherein the processing includes heating the copolymer such that the copolymer undergoes crosslinking to form the resultant thermoset polymer.

17. A method of preparing an implantable medical device comprising:
processing a copolymer prepared according to claim 1 to form at least part of the implantable medical device, wherein the processing includes heating the copolymer such that the copolymer undergoes crosslinking to form a resultant thermoset polymer that is part of the implantable medical device.

18. A method according to claim 17, wherein:
the implantable medical device comprises an intraocular lens.

* * * * *